United States Patent [19]

Kimler et al.

[11] Patent Number: 5,296,450

[45] Date of Patent: Mar. 22, 1994

[54] WATER DISPERSIBLE GRANULAR HERBICIDAL COMPOSITIONS COMPRISING DINITROANILINE HERBICIDES, MONTMORILLONITE CARRIER, AND A BASE

[75] Inventors: Joseph Kimler, Yardville; Robert Kubisch, Martinsville, both of N.J.

[73] Assignee: American Cyanamid Company, Wayne, N.J.

[21] Appl. No.: 996,412

[22] Filed: Dec. 23, 1992

[51] Int. Cl.$^5$ .................. A01N 25/08; A01N 33/18
[52] U.S. Cl. .................. 504/116; 504/333; 504/347; 71/DIG. 1
[58] Field of Search .................. 504/333, 347, 116; 71/DIG. 1

[56] References Cited

U.S. PATENT DOCUMENTS

| | | | |
|---|---|---|---|
| 4,007,258 | 2/1977 | Cohen et al. | 71/DIG. 1 |
| 4,162,154 | 7/1979 | Gates et al. | 504/333 |
| 4,511,395 | 4/1985 | Misselbrook | 71/121 |
| 4,657,582 | 4/1987 | Huber | 504/347 |
| 5,019,155 | 5/1991 | Kimpara et al. | 71/121 |
| 5,180,420 | 1/1993 | Katayama et al. | 504/116 |

*Primary Examiner*—Richard L. Raymond
*Assistant Examiner*—S. Mark Clardy
*Attorney, Agent, or Firm*—Michael P. Morris

[57] ABSTRACT

The present invention relates to water dispersible granular compositions comprising a dinitroaniline herbicide and a dispersion enhancing agent and to a process for the preparation of said compositions. Such compositions are storage stable and contain desirable dispersion properties.

16 Claims, No Drawings

WATER DISPERSIBLE GRANULAR HERBICIDAL COMPOSITIONS COMPRISING DINITROANILINE HERBICIDES, MONTMORILLONITE CARRIER, AND A BASE

BACKGROUND OF THE INVENTION

Water dispersible granules (WDG's) are becoming increasingly important in the formulation of agricultural compositions because they are more safely handled and environmentally friendly. For example, chemical spills of WDG's are easily cleaned, no toxic solvents are present in the WDG formulation, and it is possible to package WDG's in water soluble packaging, thus reducing user exposure.

The typical processes for making WDG's are pan granulation, spray drying, fluid bed granulation, and mixing agglomeration. The choice of which process to use depends on several factors, including the physical and chemical properties of the active ingredient(s), environmental and safety aspects, and volume and packaging requirements.

Pan granulation produces compositions having good dispersibility and can be used for low-melt, active ingredients. The disadvantage of pan granulation is that the granules are often dusty, and the size distribution of the granule is difficult to control. Spray drying produces compositions in high volume and good dispersibility, however the bulk density of the product is usually low and it is difficult to spray dry low-melt, active ingredients. Fluid bed granulation has basically the same advantages/disadvantages as spray drying, while mixing agglomeration has similar advantages/disadvantages as pan granulation.

The inert components of a typical prior art WDG formulation include a wetting agent, a suspension agent, a disintegrating agent and a carrier. Some commonly used wetting agents are sodium dioctyl sulfosuccinate, sodium dodecylbenzyl sulfonate, sodium lauryl sulfonate. Suspension agents are usually high molecular weight ionic compounds such as alkyl naphthalene sulfonates or lignosulfonates. Salts, such as sodium chloride, sodium sesquicarbonate, and sodium acetate are often used as disintegrating aids. A wide range of carriers can be used. The most commonly used carriers are kaolin, diatomite, attapulgite, montmorillonite, bentonite and calcite.

Dinitroaniline herbicides, which are useful for the selective control of certain grasses and broadleaf weeds, have typically been formulated as emulsifiable concentrates, flowables, wettable powders or the like, which are diluted in a tank mix. These formulations, however, require handling, measuring and mixing prior to application. Attempts have been made, therefore, to prepare granular formulations which do not require the additional handling and attendant exposure before application to the soil.

Conventional dispersible granular compositions containing dinitroaniline herbicides have been difficult to prepare. Such herbicides, which are solid at room temperature but have melting points below 100° C., have a tendency to cake, fuse or lump up when stored at or exposed to elevated temperatures, due to the excessive softening or partial melting of the herbicides. Moreover, they are often dusty and may cause staining.

In general, the above referred-to conventional dispersible granular compositions are prepared by blending and milling the appropriate amount of the selected dinitroaniline herbicide, a conventional inert carrier and one or more wetting and/or suspension agent(s), and optionally a disintegrating agent, followed by granulating the blend in the appropriate equipment using a binder solution as the granulating agent.

Efforts to produce stable granular formulations of such dinitroaniline herbicides without the drawbacks discussed above, and capable of uniform distribution, have been tried (see, e.g., U.S. Pat. No. 5,019,155). Efforts to prepare water dispersible granular compositions containing dinitroaniline herbicides with increased thermal stability have also been tried (see, e.g., U.S. Pat. No. 4,511,395). Efforts to improve dispersibility of a dinitroaniline-containing herbicidal composition in a solvent-free, WDG formulation, however, continue.

It is therefore an object of this invention to provide a solvent-free, water dispersible granular composition with improved dispersion properties.

It is also an object of this invention to provide a water dispersible granular composition comprising a novel dispersion enhancing agent.

It is another object of this invention to produce a non-dusting, non-staining, water dispersible granular composition having granules of substantially uniform size and density.

It is yet another object of this invention to provide storage stable water dispersible granular compositions.

It is a further object of this invention to provide a novel method for producing water dispersible granular compositions.

These and other objects of the invention will become more evident in the detailed description that follows.

SUMMARY OF THE INVENTION

The present invention relates to water dispersible granular compositions comprising a dinitroaniline herbicide and a dispersion enhancing agent, and to a process for the preparation of said compositions. Such compositions are storage stable and contain desirable dispersion properties.

DETAILED DESCRIPTION OF THE INVENTION

This invention provides a novel formulation of useful dinitroaniline herbicides as water dispersible granular compositions (WDG's), which offer ease of handling coupled with reduced dusting, and other environmentally desirable characteristics.

A primary concern when formulating WDG's is that the granules disperse in an acceptable amount of time, of the conventional carriers mentioned above, bentonite has been considered among the least desirable with which to formulate a WDG because the granules often are difficult to disperse. However, it has now been found that extruding the WDG with a dispersion enhancing agent permits the use of bentonite because of its compatibility with low-melt, active ingredients, such as dinitroaniline compounds. Advantageously, the use of bentonite minimizes the loss of the physical performance attributes of low-melt, active ingredients, such as dinitroanilines, compared to most other typical carriers.

As used herein, the term "dispersion enhancing agent" means a chemical entity that facilitates the swelling and dispersing of the bentonite or other suitable carrier component of the WDG composition of the invention. Typically, such dispersion enhancing agents are selected from bases, such as alkali metal hydroxides, ammonium hydroxides and amines, and water swellable polymers.

In a preferred embodiment, the present invention relates to water-dispersible granular compositions containing dinitroaniline herbicides of structural formula (I)

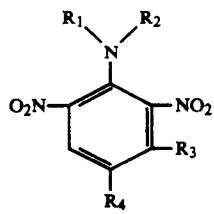

wherein $R_1$ is selected from H, $C_1$-$C_4$ straight or branched-chain alkyl, $C_3$-$C_4$alkenyl and $C_3$-$C_4$alkynyl; $R_2$ is selected from $C_1$-$C_6$ straight or branched-chain alkyl and optionally substituted with Cl or $OCH_3$, $C_3$-$C_4$alkenyl, and $C_3$-$C_4$alkynyl; $R_3$ is H, $CH_3$ or $CH_2OCH_3$; and $R_4$ is $C_1$-$C_4$alkyl, $CF_3$ or Cl. The present invention also relates to methods of producing WDG compositions containing such compounds.

More preferred formula (I) herbicides for use in the compositions of the invention include pendimethalin (N-(1-ethylpropyl)2,6-dinitro-3,4-xylidine) and trifluralin (N,N-dipropyl-2,6-dinitro-4-trifluoromethylaniline), as well as benfluralin, isopropalin, ethalfluralin, oryzelan (Ryzelan) and the like, alone, or in combination. Pendimethalin and trifluralin are most preferred.

In general, WDG's containing high concentrations of between about 20% and 90%, preferably between about 30% and 70% by weight, of low-melting dinitroanilines, such as pendimethalin and trifluralin, in combination with bentonite may be prepared in a controlled manner by extrusion in the presence of a dispersion enhancing agent, such as a base, to yield essentially dust-free and uniformly granular WDG's possessing good dispersibility. Compositions containing such high concentrations of active ingredients provide the environmental and commercial advantage of using less material to obtain the desired result. Lower concentration pesticidal compositions, however, may also be prepared, as can compositions containing mixtures of active ingredients, depending on the needs of the particular application.

The finding that bentonite clay is suitable for preparing heat-stable, water dispersible granular compositions containing high concentrations of low melting materials is unexpected. It is contemplated that the incorporation of between about 0.5% and 20% by weight, preferably between about 1% and 10% by weight, of a base, such as sodium hydroxide, potassium hydroxide, ammonium hydroxide or isopropyl amine, into the WDG formulation causes the bentonite or other suitable hydrous carrier to swell upon contact with the water. Advantageously, this swelling permits the WDG to disperse more quickly.

Carriers suitable for use in the preparation of the water dispersible granular compositions of the invention include swelling clays such as kaolinate, zeolite and preferably, montmorillonite clays, such as beidellite, bentonite, nontronite and saponite. Most preferred are carriers comprising bentonite, at least in greater part, as carrier combinations may be employed. Commercially available, naturally occurring swelling clays include VOLCLAY® Wyoming Bentonites, VEEGUM®, or other naturally occurring swelling clays which contain the same montmorillonite unit structure and properties.

Suitable wetting agents for use in the preparation of the WDG compositions of the invention include conventional agents such as sodium N-methyl-N-oleyoyltaurate (Igepon® T-77), octylphenoxy polyethoxy ethanol, nonylphenoxy polyethoxy ethanol, sodium dioctyl sulfosuccinate, sodium dodecyl benzyl sulfonate, sodium lauryl sulfonate, and the like, or mixtures thereof. Suitable suspension agents include conventional agents such as sodium lignosulfonate, alkyl naphthalene sulfonates, the sodium salt of a naphthalene sulfonic acid-formaldehyde condensate (Mowet® D-425 or Lowmar® PW), and the like, or mixtures thereof. Suitable antifoaming agents include conventional detergents such as sodium tallowate (Foamaster Soap L®) and the like. Suitable flow agents include conventional agents such as fumed silica, calcium silicate (Micro-Cel® E), and the like, or mixtures thereof.

The WDG compositions of the invention comprise about 20 to 90% by weight (preferably 30-70%) of a dinitroaniline compound, preferably a dinitroaniline compound of formula (I), admixed with from about 5.0 to 25.0% by weight of one or more carriers, about 1.0-7.5% by weight of one or more wetting agents, about 2-10% by weight of one or more suspension agents, and about 0.5-20% by weight of one or more dispersion enhancing agents. More preferably, the WDG compositions of the invention also include up to about 1% by weight of one or more antifoaming agents, and up to about 7.5% by weight of one or more flow agents to facilitate the extrusion process.

The hardness, sorptivity, particle size and apparent density of the WDG composition can be adjusted by varying or combining the type(s) of clay, the type(s) of surfactants and/or wetting agents, and mixtures thereof, which are commonly employed in agricultural formulations. Other conventional formulating agents, such as disintegrating aids or thickening agents, may also be added to the WDG compositions of the invention while maintaining the desirable properties described above.

In order to prepare the WDG compositions of the invention, the appropriate dinitroaniline technical material, or combinations thereof, is passed through a pin mill. The milled technical is then blended with the wetting agents, the suspension agents, and the carriers, and optionally, the antifoaming agents and the flow agents. The blended material is milled in an air classifier mill under liquid nitrogen or other unreactive refrigerant source sufficient to cool the mill. The milled material is then mixed with water (10-15% of total batch size) and the dispersion enhancing agents, and extruded through a conventional LUWA bench top basket extruder, for example, one having about a 0.6 mm to 1.2 mm aperture. The extruded granules are allowed to dry overnight in a hood until the residual moisture is reduced to about 1-3%. The granules are then sieved through a #16 and #40 mesh screen and collected.

The present invention is further illustrated by the following non-limiting examples.

EXAMPLES

Experimental Procedures

The preparation of WDG compositions of the invention for comparison testing with prior art compositions involved (a) milling about 20% to 90% by weight of a dinitroaniline herbicide; (b) blending the milled dinitroaniline herbicide with about 1% to 7.5% by weight of one or more wetting agents, about 2% to 10% by weight of one or more suspension agents and about 5.0 to 25.0% by weight of one or more carriers; (c) milling the blend produced by step (b) in the presence of an unreactive refrigerant sufficient to cool the mill; (d) mixing about 0.5% to 20% by weight of one or more dispersion enhancing agents with water, and the milled blend produced by step (c); (e) extruding the milled blend into granular compositions; and (f) drying and extruded granular compositions.

Following the above procedures, the following WDG compositions were prepared and tested. The important physical properties of the WDG compositions of Examples 1–4 are set forth in Examples 5–6.

EXAMPLES 1–4

| Ingredient (% wt./wt.) | EXAMPLES 1–4 | | | |
|---|---|---|---|---|
| | 1 | 2 | 3 | 4 |
| Pendimethalin Tech. (91%) | 66.7 | 66.0 | 66.0 | 66.3 |
| Calcium Silicate | 5.0 | 5.0 | 5.0 | 5.0 |
| Sodium-N-Methyl-N-Oleoyltaurate | 2.5 | 2.5 | 2.5 | 2.5 |
| Sodium Naphthalene Formaldehyde Sulfonate, condensate | 5.0 | 5.0 | 5.0 | 5.0 |
| Bentonite Clay | 16.0 | 15.7 | 15.7 | — |
| Kaolin Clay | 4.3 | 4.3 | 4.3 | 20.7 |
| Sodium Tallowate | 0.5 | 0.5 | 0.5 | 0.5 |
| Sodium Hydroxide | — | 1.0 | — | — |
| Sodium Chloride | — | — | 1.0 | — |

EXAMPLE 5

Evaluation of Dispersibility and Temperature Stability of the Test Compositions

Test compositions are stored at room temperature, 45° C. or 50° C. for 7 days prior to evaluation. A predetermined amount of test composition, typically 1 gram of quantity sufficient to represent the maximum end use concentration, is added to 100 mL of water in a graduated cylinder, which is then quickly stoppered. The cylinder is immediately rotated (inverted) 180°, and, after a 3 second pause, rotated an additional 180°, and held for 3 seconds. The cycle is then repeated. The number of 360° cycles required to completely dissolve/-disperse the granules is recorded. The procedure is continued until 30 inversions have been made. The desired quick dispersion of the granules is reflected by the lower number of inversions (Table 1).

TABLE 1

| | Dispersibility (Number of Inversions - lower the number the better) | | |
|---|---|---|---|
| Example | 7 days @ RT | 7 days at 45° C. | 7 days @ 50° C. |
| 1 | 18 | 17 | 20 |
| 2 | 12 | 11 | 11 |
| 3 | 5 | 14 | 12 |
| 4 | 22 | 23 | 28 |

EXAMPLE 6

Evaluation of Suspendibility of Test Composition

Test compositions are stored at room temperature, 45° C. or 50° C., for 7 days prior to evaluation. A predetermined amount of test composition is dispersed in a controlled aqueous system and allowed to settle for 30 minutes. An aliquot is taken from center of the suspension and the solids content is measured. (This does not account for dissolved solids in the dilution water, or the residual moisture retained in the dried solids or picked up by hygroscopic solids).

TABLE 2

| | Suspensibility (% Suspended - higher the number the better) | | |
|---|---|---|---|
| Example | 7 days @ RT | 7 days at 45° C. | 7 days @ 50° C. |
| 1 | 85.6 | 84.9 | 68.2 |
| 2 | 82.2 | 83.5 | 68.8 |
| 3 | 29.6 | — | — |
| 4 | 86.9 | 22.2 | 17.8 |

As the results demonstrate, the WDG compositions of the invention possess improved dispersibility and suspendibility compared to the prior art formulations.

Many variations of this invention will occur to those skilled in the art in light of the above, detailed description. For example, instead of using sodium hydroxide as the dispersion enhancing agent, a water swellable polymer may be used. All such obvious variations are within the full intended scope of the appended claims.

We claim:

1. A water dispersible granular composition comprising on a weight to weight basis about 20% to 90% of a dinitroaniline herbicide; about 5% to 25% of a montmorillonite carrier; about 1.0% to 7.5% of a wetting agent; about 2% to 10% of a suspension agent; and about 0.5% to 20% of a base selected from the group consisting of amines and alkali metal hydroxides.

2. The water dispersible granular composition according to claim 1 wherein the base is selected from the group consisting of sodium hydroxide, potassium hydroxide, and isopropyl amine.

3. The water dispersible granular composition according to claim 2 wherein the base is sodium hydroxide.

4. The water dispersible granular composition according to claim 1, further comprising up to about 1% by weight of an antifoaming agent and up to about 7.5% by weight of a flow agent.

5. The water dispersible granular composition according to claim 1 wherein the dinitroaniline herbicide is selected from the group consisting of pendimethalin, trifluralin, isopropalin, ethalfluralin, benfluralin and oryzalin.

6. The water dispersible granular composition according to claim 5 wherein the dinitroaniline herbicide is selected from pendimethalin and trifluralin.

7. The water dispersible granular composition according to claim 1 comprising on a weight to weight basis about 30% to 70% of a dinitroaniline herbicide.

8. The water dispersible granular composition according to claim 1 wherein the carrier is selected form the group consisting of beidellite, bentonite, nortronite, saponite, and mixtures thereof.

9. The water dispersible granular compositions according to claim 8 wherein the carrier comprises bentonite.

10. A method for the production of a dinitroaniline-containing water dispersible granular composition comprising the steps of:
(a) milling about 20% to 90% by weight of a dinitroaniline herbicide;
(b) blending the milled dinitroaniline herbicide with about 1% to 7.5% by weight of one or more wetting agents, about 2% to 10% by weight of one or more suspension agents and about 5% to 25% by weight of one or more montmorillonite carriers;

(c) milling the blend produced by step (b) in the presence of an unreactive refrigerant sufficient to cool the mill;

(d) mixing about 0.5% to 20% by weight of one or more bases selected from the group consisting of amines and alkali metal hydroxides with water and the milled blend produced by step (c);

(e) extruding the milled blend into granular compositions; and (f) drying the extruded granular compositions.

11. The method according to claim 10 wherein the dinitroaniline herbicide is selected from the group consisting of pendimethalin, trifluralin, isopropalin, ethalfluraline, benfluralin and oryzalin.

12. The method according to claim 10 wherein the dinitroaniline herbicide is selected from pendimethalin and trifluralin.

13. The method according to claim 10 wherein step (b) further comprises the addition of up to about 1% by weight of one or more antifoaming agents and up to about 7.5% by weight of one or more flow agents.

14. The method according to claim 10 wherein the base is selected from the group consisting of sodium hydroxide, potassium hydroxide and isopropyl amine.

15. The method according to claim 14 wherein the base is sodium hydroxide.

16. The method according to claim 10 wherein the granular compositions produced by step (c) are dried until the residual moisture is reduced to about 1%–3%.

* * * * *